United States Patent
Nishiguchi (10) Patent No.: US 10,281,433 B2
(45) Date of Patent: May 7, 2019

(54) MASS SPECTROMETER AND ION MOBILITY SPECTROMETER

(71) Applicant: SHIMADZU CORPORATION, Kyoto-shi, Kyoto (JP)

(72) Inventor: Masaru Nishiguchi, Osaka (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/545,405

(22) PCT Filed: Jan. 22, 2015

(86) PCT No.: PCT/JP2015/051622
§ 371 (c)(1),
(2) Date: Jul. 21, 2017

(87) PCT Pub. No.: WO2016/117066
PCT Pub. Date: Jul. 28, 2016

(65) Prior Publication Data
US 2018/0011057 A1    Jan. 11, 2018

(51) Int. Cl.
*H01J 49/00* (2006.01)
*G01N 27/62* (2006.01)
(Continued)

(52) U.S. Cl.
CPC ........ *G01N 27/622* (2013.01); *G01N 27/62* (2013.01); *H01J 49/0445* (2013.01);
(Continued)

(58) Field of Classification Search
CPC ........ H01J 49/00; H01J 49/02; H01J 49/0404; H01J 49/0409; H01J 49/0431;
(Continued)

(56) References Cited

U.S. PATENT DOCUMENTS 5,412,208 A    5/1995    Covey et al.
2005/0072934 A1    4/2005    Frazer et al.
(Continued)

FOREIGN PATENT DOCUMENTS

| | | |
|---|---|---|
| CN | 1959401 A | 5/2007 |
| EP | 1 739 720 A2 | 1/2007 |
| WO | 2009/124298 A2 | 10/2009 |

OTHER PUBLICATIONS

Ching Wu et al., "Separation of Isomeric Peptides Using Electrospray Ionization/High-Resolution Ion Mobility Spectrometry," Analytical Chemistry, Jan. 15, 2000, pp. 391-395, vol. 72, No. 2.
(Continued)

*Primary Examiner* — Jason L McCormack
(74) *Attorney, Agent, or Firm* — Sughrue Mion, PLLC (57) ABSTRACT

A cylindrically-shaped auxiliary electrode and a cylindrically-shaped reflecting electrode are located anterior to a spray flow ejected from an ESI ionization probe. An inlet end of a heated capillary extends into the space between the two electrodes. The auxiliary electrode and heated capillary are grounded, while the reflecting electrode is supplied with a direct-current voltage having the same polarity as measurement target ions. As a result, a reflecting electric field which reflects ions originating from sample components and charged droplets, being carried by the spray flow, is created within the space between the two electrodes. A focusing electric field for focusing ions onto the inlet end is also created in an area near the inlet end. The ions originating from sample components are thereby separated from the gas flow and gathered around the inlet end, to be drawn into the heated capillary and sent into a vacuum chamber.

10 Claims, 6 Drawing Sheets

(51) Int. Cl.
*H01J 49/06* (2006.01)
*H01J 49/16* (2006.01)
*H01J 49/04* (2006.01)

(52) U.S. Cl.
CPC .......... *H01J 49/061* (2013.01); *H01J 49/067* (2013.01); *H01J 49/165* (2013.01)

(58) Field of Classification Search
CPC ...... H01J 49/0445; H01J 49/045; H01J 49/10; H01J 49/165; H01J 49/167
USPC .................. 250/281, 282, 285, 286, 288
See application file for complete search history.

(56) References Cited

U.S. PATENT DOCUMENTS

| | | | | |
|---|---|---|---|---|
| 2007/0023675 A1* | 2/2007 | Fischer | .............. | H01J 49/0445 250/423 P |
| 2009/0250608 A1* | 10/2009 | Mordehai | ............. | H01J 49/167 250/288 |
| 2010/0148060 A1* | 6/2010 | Panayi | ................ | H01J 49/0004 250/286 |

OTHER PUBLICATIONS

International Search Report of PCT/JP2015/051622 dated Mar. 31, 2015.
Communication dated Dec. 19, 2017 from the European Patent Office in counterpart application No. 15878760.6.
Written Opinion dated Mar. 31, 2016 in application No. PCT/JP2015/051622.
Communication dated Jun. 1, 2018, issued by the State Intellectual Property Office of People's Republic of China in counterpart application No. 201580074229.2.

* cited by examiner

Fig. 3B
REFLECTING ELECTRODE: ON (PRESENT INVENTION)

Fig. 3A
REFLECTING ELECTRODE: OFF (PRIOR ART)

MASS SPECTROMETER AND ION MOBILITY SPECTROMETER

CROSS REFERENCE TO RELATED APPLICATIONS

This application is a National Stage of International Application No. PCT/JP2015/051622 filed Jan. 22, 2015, the contents of which are incorporated herein by reference in its entirety.

TECHNICAL FIELD

The present invention relates to a mass spectrometer and ion mobility spectrometer, and more specifically, to a mass spectrometer and ion mobility spectrometer having an ion source for ionizing ions in a liquid sample by spraying the sample into an ambience of substantially atmospheric pressure.

BACKGROUND ART

In a liquid chromatograph mass spectrometer (LC-MS) in which a mass spectrometer is used as the detector for a liquid chromatograph (LC), an ion source which employs an atmospheric pressure ionization method, such as electrospray ionization (ESI), atmospheric pressure chemical ionization (APCI) or atmospheric pressure photoionization (APPI), is used to ionize a compound in a liquid sample. In a mass spectrometer employing such an atmospheric pressure ion source, ions generated within an ionization chamber in which an ambience of substantially atmospheric pressure is present need to be introduced into a vacuum chamber in which a vacuum atmosphere is maintained. To improve the sensitivity of the analysis, it is particularly important: to increase the amount of ions generated within the ionization chamber, and to improve the efficiency of introducing ions from the ionization chamber into the vacuum chamber.

A commonly known technique aimed at increasing the amount of ions generated within an ESI ion source, which is a typically used atmospheric pressure ion source, is to supply a stream of heated gas onto electrically charged droplets sprayed from an ionization probe to promote desolvation of those droplets. For example, in a device described in Patent Literature 1, a stream of heated gas is supplied so as to intersect with the moving path of the charged droplets sprayed from the ionization probe. In another device, described in Patent Literature 2, a stream of heated gas is ejected in a hollow cylindrical form coaxially with the flow of the charged droplets sprayed from the ionization probe; i.e. the flowing direction of the heated gas is the same as the moving direction of the charged droplets. Both of these configurations have been proven to be effective for increasing the amount of ions to be generated. At the moment, desolvation techniques using heated gas based on one of the two aforementioned systems are adopted in almost all commercially offered mass spectrometers equipped with atmospheric pressure ion sources, In an ospheric pressure ion source, the arrangement of the ionization probe and an ion introduction section (e.g. ion introduction tube or sampling cone) is normally determined so that the spraying direction of the droplets from the ionization probe extends orthogonally or obliquely to the direction of introducing ions into the vacuum chamber, in order to prevent large droplets among the sample droplets sprayed from the ionization probe from being introduced into the vacuum chamber. The ions generated from the sample droplets are drawn into the ion introduction section and carried into the vacuum chamber by a stream of gas flowing from the ionization chamber into the ion introduction section mainly due to the differential pressure between the two ends of the ion introduction section.

The direction of the aforementioned heated gas ejected for promoting the desolvation is normally different from that of the gas stream flowing into the ion introduction section produced by the differential pressure. Therefore, the stream of heated gas has no effect of increasing the amount of gas stream flowing into the ion introduction section. In the case of the configuration described in Patent Literature 2, the stream of heated gas may be a gas stream which is orthogonal to the ion introduction direction in an area near the ion introduction port, i.e. a gas stream which flows in a direction which interferes with the introduction of the ions. Although the heated gas is effective for increasing the amount of ion generation, it cannot be considered to be effective from the viewpoint of improving the efficiency of introducing ions from the ionization chamber into the vacuum chamber.

One method for improving the ion introduction efficiency is proposed in Patent Literature 2, in which a voltage applied to the ion introduction port is adjusted to create an appropriate electric field near the ion introduction port so that the ions near the ion introduction port will be attracted and collected into the same port by the effect of the electric field. However, according to a study by the present inventor, the electric field created near thee ion introduction port by such a system is not strong enough to sufficiently collect the ions against the powerful stream of heated gas flowing in the orthogonal direction to the ion introduction direction. Accordingly, even with such an electric field, it is difficult to significantly improve the efficiency of introducing the ions from the ionization chamber into the vacuum chamber.

CITATION LIST

Patent Literature

Patent Literature 1: U.S. Pat. No. 5,412,208 A
Patent Literature 2: WO 2009/124298 A

Non Patent Literature

Non Patent Literature 1: Ching Wu and three other authors, "Separation of Isomeric Peptides Using Electrospray Ionization/High-Resolution Ion Mobility Spectrometry", Anal. Chem., 2000, Vol. 72, pp. 391-395

SUMMARY OF INVENTION

Technical Problem

As described thus far, in conventional mass spectrometers using atmospheric pressure ion sources, increasing the amount of ions generated in the ambience of atmospheric pressure is considered to be more important for improving the sensitivity of the analysis. An efficient introduction of the generated ions into the vacuum chamber has not always been sufficiently considered, which poses the problem that a considerable proportion of the generated ions are wasted.

The present invention has been developed to solve the previously described problem. Its primary objective is to provide a mass spectrometer capable of improving the sensitivity of an analysis by efficiently introducing ions generated in an ambience of atmospheric pressure into a vacuum chamber with minimum waste of the ions.

Solution to Problem

The mass spectrometer according to the present invention developed for solving the previously described problem is a mass spectrometer provided with: an ion source including an ionization probe for spraying a liquid sample into an ionization chamber in which an ambience of atmospheric pressure is present; and an ion introduction section for sending, from the ionization chamber to a vacuum chamber, ions generated by the ion source from a component contained in sample droplets sprayed from the ionization probe, where the arrangement of the ionization probe and the ion introduction section is determined so that the spraying direction of the liquid sample from the ionization probe extends orthogonally or obliquely to the direction of introducing the ions from the ionization chamber by the ion introduction section, the mass spectrometer including:

a) an auxiliary electrode provided in the spraying direction of the sample droplets from the ionization probe and at a closer position than the inlet end of the ion introduction section, the auxiliary electrode surrounding the central axis of a spray flow from the ionization probe;

b) a reflecting electrode provided in the spraying direction of the sample droplets from the ionization probe and at a farther position than the inlet end of the ion introduction section, the reflecting electrode surrounding the central axis of the spray flow from the ionization probe; and c) a voltage supplier for applying, to the reflecting electrode, a voltage determined with reference to the potential of the auxiliary electrode so that a measurement target ion is reflected by the reflecting electrode.

In the mass spectrometer according to the present invention, for example, the ion source is an ESI, APCI or APPI ion source, If the ion source is an ESI ion source, a predetermined level of high direct-current voltage for electrically charging the liquid sample is applied to the tip portion of the ionization probe. If the ion source is an APCI ion source, a discharge electrode for inducing corona discharge for generating buffer ions is provided within or in the vicinity of the space between the ionization probe and the auxiliary electrode. If the ion source is an APPI ion source, a light source for irradiating, with ultraviolet or other kinds of light, the spray flow passing through the space between the point of ejection from the ionization probe and the auxiliary electrode.

In the mass spectrometer according to the present invention, as viewed from the tip of the ionization probe in the spraying direction of the sample droplets, the auxiliary electrode is located at the closest position, beyond which the reflecting electrode is located, with the open end of the ion introduction section arranged so that its opening is located in the space between the auxiliary and reflecting electrodes. Each of the auxiliary and reflecting electrodes may typically be shaped like a hollow circular cylinder, hollow polygonal cylinder or similarly-shaped object. Those hollow cylindrical objects may have a cut portion in its circumferential direction. The ion introduction section is typically an ion introduction tube, such as an electrically conductive capillary. In that case, the inlet end of the ion introduction tube should preferably extend into the space between the space surrounded by the auxiliary electrode and that surrounded by the reflecting electrode.

The auxiliary electrode and the ion introduction section are connected, for example, to a ground, while the voltage supplier applies, to the reflecting electrode, a predetermined level of direct-current voltage with the polarity selected according to the polarity of the measurement target ion. Due to the potential difference between the potential of the reflecting electrode and the potential of the auxiliary electrode and the ion introduction section (ground potential), a reflecting electric field having the effect of repelling the ions and electrically charged micro droplets (in the case of the ESI ion source) generated from the droplets sprayed from the ionization probe is created within the space surrounded by the reflecting electrode as well as within the space between the reflecting and auxiliary electrodes. Additionally, a focusing electric field having the effect of focusing those ions and charged droplets onto the inlet end of the ion introduction section is created within a local space between the reflecting electrode and the inlet end of the ion introduction section. The strengths of the reflecting and focusing electric fields can be regulated via the voltage applied to the reflecting electrode. By applying a certain high level of voltage to the reflecting electrode, the ions and electrically charged micro droplets can be separated from the stream of gas forming the spray flow (or the like) and attracted to the inlet end of the ion introduction section. In this manner, the ions generated within the ionization chamber can be efficiently guided to the ion introduction section and carried into the vacuum chamber through the ion introduction section even when there is a gas stream of a certain strength in an area near the inlet end of the ion introduction section.

In the mass spectrometer according to the present invention, the auxiliary electrode may be equipped with a gas ejector for ejecting gas from outside the spray flow ejected from the ionization probe, toward the central axis of the same spray flow, in a manner to surround the spray flow by the gas.

In this configuration, the stream of gas ejected from the gas ejector interferes with the gas stream forming the spray flow from the ionization probe, whereby the gas stream from the ionization probe is weakened. As a result, the ions in the spray flow can be more easily separated from the stream of gas by the effect of the reflecting and focusing electric fields, so that the efficiency of collecting the ions to the inlet end of the ion introduction section will be further improved.

The moving speed of an ion within the ionization chamber in which both the gas stream and the electric field are present in an ambience of substantially atmospheric pressure depends on the mobility of the ion. The ion mobility in turn depends on the mass, valence, collision cross-section with neutral particles (e.g. residual gas molecules) and other properties of the ion. Therefore, from the viewpoint of the efficiency for an ion to successfully reach the inlet end of the ion introduction section, the optimum strengths of the reflecting and focusing electric fields change depending on the mass-to-charge ratio of the ion. In other words, changing the strengths of the reflecting and focusing electric fields by applying a different voltage to the reflecting electrode results in a change in the mass-to-charge ratio of the ion which efficiently reaches the inlet end of the ion introduction section.

Accordingly, in the mass spectrometer according to the present invention, the voltage supplier may preferably be configured to change the applied voltage to the reflecting electrode according to the mass-to-charge ratio of the measurement target ion.

For example, in the case of performing a scan measurement over a predetermined range of mass-to-charge ratios using a quadrupole mass filter as the mass separator, it is preferable to continuously change the applied voltage to the reflecting electrode synchronously with the operation of continuously changing the applied voltage to the quadrupole mass filter during the scan measurement.

In this configuration, the efficiency of introducing the ions from the ionization chamber into the vacuum chamber can be improved for any mass-to-charge ratio of the measurement target ion.

As noted earlier, changing the strengths of the reflecting and focusing electric fields by applying a different voltage to the reflecting electrode results in a change in the mass-to-charge ratio of the ion which efficiently reaches the inlet end of the ion introduction section. This means that it is possible to realize a function which corresponds to a differential mobility analyzer for separating electrically charged particles according to their electrical mobilities.

Thus, an ion mobility spectrometer according to the present invention includes:

a) an ion source including an ionization probe for spraying a liquid sample into an ambience of atmospheric pressure;

b) an ion detector located anterior to a spray flow from the ionization probe, for detecting ions generated by the ion source from a component contained in sample droplets sprayed from the ionization probe;

c) an auxiliary electrode provided in the spraying direction of the sample droplets from the ionization probe and at a closer position than the ion detector, the auxiliary electrode surrounding the central axis of a spray flow from the ionization probe;

d) a reflecting electrode provided in the spraying direction of the sample droplets from the ionization probe and at a farther position than the ion detector, the reflecting electrode surrounding the central axis of the spray flow from the ionization probe; and e) a voltage supplier for applying, to the reflecting electrode, a voltage determined with reference to the potential of the auxiliary electrode so that a measurement target ion is reflected by the reflecting electrode.

In the ion mobility spectrometer according to the present invention, for example, the auxiliary electrode is grounded, while the voltage supplier changes the applied voltage to the reflecting electrode according to a predetermined sequence. This operation induces a temporal change in the strength of the reflecting electric field within the space surrounded by the reflecting electrode as well as within the space between the reflecting and auxilary electrodes, and this change in turn causes a change in the ion mobility of the ion which can most efficiently reach the ion detector. Accordingly, it is possible to obtain an ion mobility spectrum which roughly shows the relationship between the ion mobility and the ion intensity, based on the detection signals produced by the ion detector. Alternatively, the voltage applied from the voltage supplier to the reflecting electrode may be fixed at a predetermined level to selectively detect an ion having a specific ion mobility, in which case, for example, a chromatogram showing a temporal change in the intensity of that ion can be obtained.

In the present ion mobility spectrometer, if the spray flow ejected from the ionization probe is too strong, ions cannot be duly reflected even by a reflecting electric field having a certain strength, causing a problem in the separation of the ions according to their ion mobilities. To address this problem, in the ion mobility spectrometer according to the present invention, the auxiliary electrode may be equipped with a gas ejector for ejecting gas from outside the spray flow ejected from the ionization probe, toward the central axis of the same spray flow, in a manner to surround the spray flow by the gas.

In this configuration, the stream of gas ejected from the gas ejector interferes with the gas stream forming the spray flow from the ionization probe, whereby the gas stream from the ionization probe is weakened. As a result, the ions in the spray flow are more likely to individually undergo the effect of the reflecting electric field according to their ion mobilities and eventually reach the ion detector at different timings according to their ion mobilities. Consequently, the ion-mobility resolving power and the detection sensitivity will be further improved.

Advantageous Effects of the Invention

In the mass spectrometer according to the present invention, ions generated within the ionization chamber in which an ambience of atmospheric pressure is present can be efficiently collected and introduced through the ion introduction section into the vacuum chamber. The amount of ions subjected to mass spectrometry is thereby increased, and the sensitivity of the analysis is improved. The ion mobility spectrometer according to the present invention has a simple configuration yet can provide an ion mobility spectrum or other forms of information, making it possible to create an ion mobility spectrometer with a smaller size, lighter weight, lower production cost and other favorable characteristics.

DESCRIPTION OF EMBODIMENTS

[First Embodiment]

Figure 1:
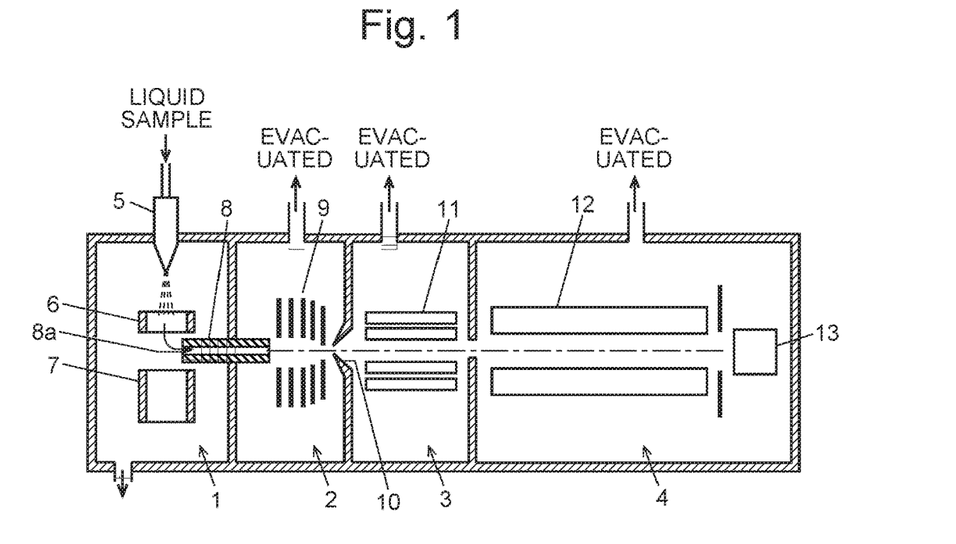
FIG. 1 is a schematic configuration diagram of a mass spectrometer as the first embodiment of the present invention.
Figure 2:
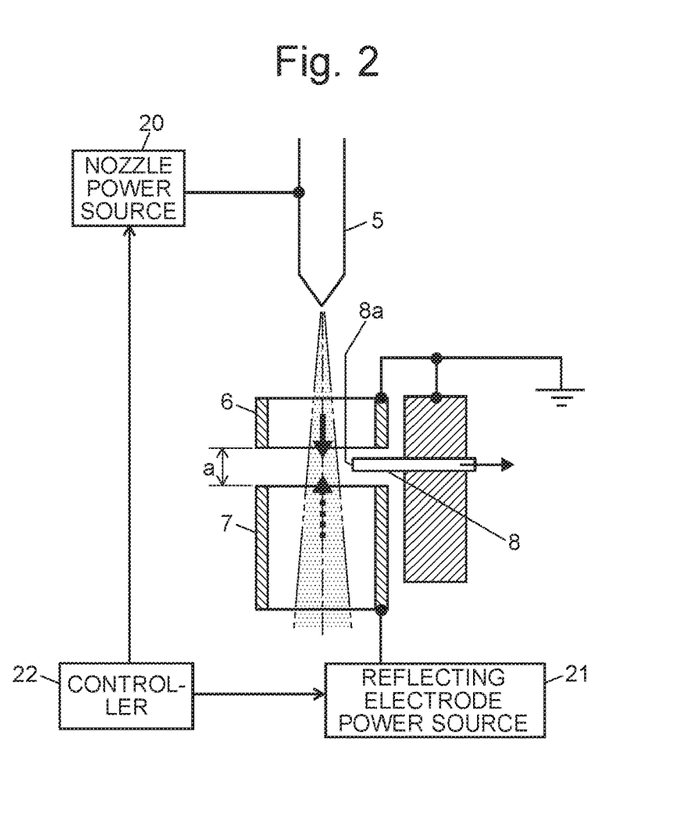
FIG. 2 is a configuration diagram of the ion source in the mass spectrometer of the first embodiment.

A mass spectrometer which is one embodiment (first embodiment) of the present invention is hereinafter described. FIG. 1 is a schematic overall configuration diagram of the mass spectrometer of the first embodiment. FIG. 2 is a configuration diagram of the ion source in the same mass spectrometer.

In FIG. 1, the ambience within an ionization chamber 1 is maintained at substantially atmospheric pressure, while the ambience within an analysis chamber 4 is maintained at a high degree of vacuum by evacuation with a high-performance vacuum pump (normally, a turbo molecular pump combined with a rotary pump). Provided between the ionization chamber 1 and the analysis chamber 4 are a first intermediate vacuum chamber 2 in which a low vacuum ambience is present and a second intermediate vacuum chamber 3 whose degree of vacuum is between the first intermediate vacuum chamber 2 and the analysis chamber 4. In other words, this mass spectrometer has the configuration of a multi-stage differential pumping system with the degree of vacuum increased in a stepwise manner from the ionization chamber 1 in the travelling direction of the ions.

Into the ionization chamber 1, a liquid sample which contains sample components is sprayed from an ESI ionization probe 5 while receiving an imbalanced polarity of electric charges. When the flow rate of the liquid sample is high, heated nebulizer gas may be ejected from a nebulizer-gas tube having a hollow cylindrical shape concentrically surrounding the sample-spraying nozzle, as described in Patent Literature 2, to assist the spraying of the sample solution. The electrically charged droplets sprayed from the tip of the ionization probe 5 are broken into finer droplets by coming into contact with the ambient gas, with the solvent vaporizing from those droplets. During this process, the sample components carrying electric charges are ejected from the droplets, forming ions. An auxiliary electrode 6 and reflecting electrode 7, which have respective functions (as will be described later), are provided anterior to the spray flow from the ionization probe 5.

The ionization chamber 1 and the first intermediate vacuum chamber 2 communicate with each other through a thin heated capillary 8, which corresponds to the ion introduction section in the present invention. There is a pressure difference between the two open ends of this heated capillary 8, and this pressure difference creates a gas stream flowing from the ionization chamber 1 into the first intermediate vacuum chamber 2 through the heated capillary 8. The ions generated from the sample components within the ionization chamber 1 are carried mainly by this gas stream and drawn into the heated capillary 8, to be ejected from the outlet end of the same capillary into the first intermediate vacuum chamber 2 along with the gas stream. A skimmer 10 having a small orifice at its apex is provided in a partition wall which separates the first intermediate vacuum chamber 2 and the second intermediate vacuum chamber 3. The first intermediate vacuum chamber 2 contains an ion guide 9 composed of multiple plate electrodes arranged around the ion beam axis. Due to the effect of the electric field created by this ion guide 9, the ions introduced into the first intermediate vacuum chamber 2 are converged onto the vicinity of the orifice of the skimmer 10, to be sent through the orifice into the second intermediate vacuum chamber 3.

The second intermediate vacuum chamber 3 contains a multipole (e.g. octapole) ion guide 11. Due to the effect of a radiofrequency electric field created by this ion guide 11, the ions are converged and sent into the analysis chamber 4. Within the analysis chamber 4, the ions are introduced into a space extending along the longitudinal axis of a quadrupole mass filter 12. Due to the effect of the electric field created by a radiofrequency voltage and direct-current voltage applied to the quadrupole mass filter 12, only ions having a specific mass-to-charge ratio are allowed to pass through the quadrupole mass filter 12 and reach an ion detector 13. The ion detector 13 produces detection signals corresponding to the amount of ions which have reached the detector, and feeds the signals to a data processing unit (not shown). By allowing the measurement target ions among the ions generated in the ionization chamber 1 to eventually enter the ion detector 13 with minimum loss of the ions, a high-sensitivity analysis can be realized.

As shown in FIG. 2, within the ionization chamber 1, an auxiliary electrode 6 is located closest to the ionization probe 5, along with a reflecting electrode 7 located farther from the ionization probe 5 and at distance a from the auxiliary electrode 6. In the present example, both auxiliary electrode 6 and reflecting electrode 7 are shaped like a hollow circular cylinder and concentrically arranged with the central axis of the spray flow from the ionization probe 5. The heated capillary 8 is provided so that its inlet end 8a projects into the space between the two electrodes 6 and 7. Accordingly, as viewed from the tip of the ionization probe 5 in the ejecting direction of the spray flow, there are the auxiliary electrode 6, inlet end 8a of the heated capillary 8, and reflecting electrode 7 arranged in the mentioned order. Additionally, as shown in FIG. 2, the spray flow which moves spreading in a substantially conical form passes through the hollow area of the a electrode 6 (the space surrounded by the auxiliary electrode 6) and that of the reflecting electrode 7 (the space surrounded by the reflecting electrode 7) in the mentioned order. In the present example, the auxiliary and reflecting electrodes 6 and 7 have the same inner diameter, although their inner diameters do not always need to be the same. The shape of the electrodes 6 and 7 may be different from a hollow circular cylinder. For example, they may be shaped like a hollow polygonal cylinder.

The auxiliary electrode 6, and the electrically conductive partition wall which is electrically connected to the heated capillary 8, are grounded, whereas the reflecting electrode 7 is supplied with a direct-current voltage from a reflecting electrode power source 21. To the ionization probe 5, a high direct-current voltage with a maximum level of approximately several kV is applied from a nozzle power source 20. The polarity of each of the voltages respectively applied to the reflecting electrode 7 and the ionization probe 5 is selected according to the polarity of the measurement target ion: when the measurement target ion is a positive ion, both voltages have the positive polarity. The voltages generated by the nozzle power source 20 and the reflecting electrode power source 21 are controlled by a controller 22.

The following description assumes that the measurement target ion is a positive ion. When the measurement target ion is a negative ion, only the polarity of the applied voltages only needs to be changed.

In general, the motion of an ion in an ambience of atmospheric pressure depends on the strength of the gas flow and that of the electric field. A macroscopic moving velocity v of an ion is given by the following equation (1), with $v_f$ denoting the velocity of the gas flow and E denoting the strength of the electric field:

$$v = v_f + KE \quad (1)$$

where K is the ion mobility. The ion mobility is a parameter which determines the moving velocity of the ion due to an electric field taking into account the collision with neutral particles. This parameter depends on the mass, valence and collision cross-section with neutral particles of the ion as well as the gas temperature and other factors. According to a report in Non Patent Literature 1, an ion having a mass-to-charge ratio (m/z) of approximately 500 has an ion mobility of $1 \times 10^{-4}$ m$^2$/Vs.

Most of the particles sprayed from the ionization probe 5 are considered to be in the form of electrically charged micro particles containing the solvent. Since those particles are larger in size than their ionized form, it is possible to consider that the mobility of those particles is lower than the value of the mobility for an ion calculated in the aforementioned manner. It can also be interred that the mobility of those charged droplets gradually becomes closer to the value of the ion, since their size decreases with the progress of the desolvation during their flight in the ambience of atmospheric pressure.

Although it depends on the device configuration or other factors, in commonly used mass spectrometers, the velocity of the gas flow ejected from the ionization probe 5 reaches several tens of m/s in an area near the inlet end 8*a* of the heated capillary 8. Provided that this gas-flow velocity near the inlet end 8*a* is 40 m/s, if an ion having the aforementioned mobility of $K=1\times10^{-4}$ m$^2$/Vs needs to be retained near the inlet end 8*a* against the gas flow, an electric field having a strength calculated by the following equation (2) needs to be created in the opposite direction to the gas flow:

$$|E|=|v_g|/K=4 \text{ kV/cm} \quad (2)$$

There is a conventional device in which, in order to attract ions and charged droplets toward the ion introduction port, a focusing electric field directed to the ion introduction port is generated by setting the potential of the ion introduction port at a lower level than a nearby electrode (e.g. the tip portion of the ionization probe). However, by this method, the strength of the electric field in the opposite direction to the gas flow cannot be easily increased to the aforementioned value. Consequently, a considerable amount of ions and charged droplets will be carried away and disposed of.

By comparison, the mass spectrometer according to the present embodiment is provided with the auxiliary and reflecting electrodes 6 and 7 for efficiently generating an electric field in the opposite direction to the gas flow. As shown by the solid arrow in FIG. 2, the spray flow ejected from the ionization probe 5 travels downward. Ions generated from the sample droplets also travel in approximately the same direction. Against this flow, a reflecting electric field which acts on the ions to repel them upward is created within the space between the auxiliary and reflecting electrodes 6 and 7 by the direct-current voltage applied from the reflecting electrode power source 21 to the reflecting electrode 7. Since the distance a between the auxiliary and reflecting electrodes 6 and 7 is comparatively short and the inlet end 8*a* of the heated capillary 8 is located within the space between the two electrodes, a strong electric field which acts on the ions in the opposite direction to the gas slow can be created in an area near the inlet end 8*a*. For example, if the distance a between the auxiliary and reflecting electrodes 6 and 7 is 5 mm, a strong electric field having the aforementioned strength of approximately 4 kV/cm can be created by applying an appropriate voltage of equal to or lower than roughly 3 kV to the reflecting electrode 7, with the leakage of the electric field considered.

Since the heated capillary 8 extending into the space between the auxiliary and reflecting electrodes 6 and 7 is also at the ground potential, a focusing electric field which acts on the ions to drive them toward the inlet end 8*a* of the heated capillary 8 will naturally be created between the inlet end 8*a* and the reflecting electrode 7.

In FIG. 2, the ions and charged droplets carried by the spray flow and travelling downward are separated from the gas flow and repelled upward due to the aforementioned strong reflecting electric field, being suspended near the inlet end 8*a* of the heated capillary 8. Then, due to the focusing electric field, they are attracted toward the vicinity of the inlet end 8*a* of the heated capillary 8. Those ions and charged droplets collected in the vicinity of the inlet end 8*a* of the heated capillary 8 are carried by the stream of gas flowing through the heated capillary 8, to be drawn into the heated capillary 8 and sent to the first intermediate vacuum chamber 2. Thus, in the mass spectrometer of the present embodiment, a large amount of ions which would be directly carried away by the gas flow and disposed of in a conventional case can he efficiently collected and sent to the next stage, whereby a larger amount of ions are subjected to mass spectrometry and high sensitivity is achieved.

To confirm the previously described effect, simulations of the gas flow and the electric field to evaluate the ion utilization efficiency were performed, the results of which are hereinafter described. A macroscopic moving velocity of an ion in a gas flow under an electric field can be approximately given by equation (1). Accordingly, the macroscopic motion of the ion can be simulated by calculating the gas-flow velocity and the electric field, and then computing the velocity field of the ions by combining the calculated gas-flow velocity and electric field. For the simulation, it was assumed that the ionization probe 5 was a commonly used ESI ionization probe having the coaxial and cylindrical heating-gas mechanism. As the elements for generating the gas flow, two gases were taken into account: a nebulizer gas for promoting the scattering and atomization of the droplets at the tip portion of the ionization probe 5, and a heated gas coaxially and cylindrically sprayed around the nebulizer gas. The flows of those gases were computed by hydrodynamic simulations. As for the auxiliary electrode 6, reflecting electrode 7 and heated capillary 8, an arrangement of as shown in FIG. 2 was assumed to simulate the electric field.

Figure 3A:
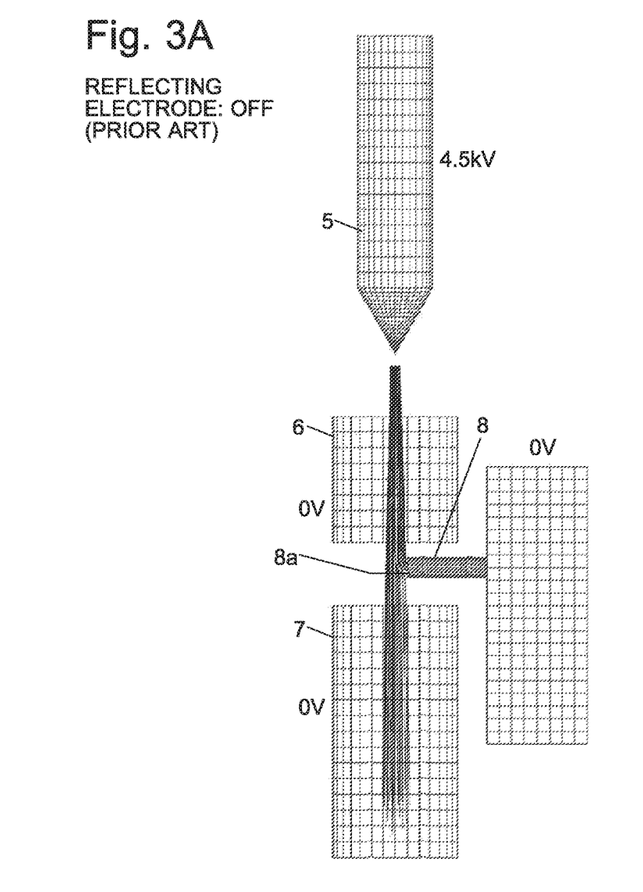
FIGS. 3A and 3B are graphics showing a simulation result of ion trajectories.
Figure 3B:
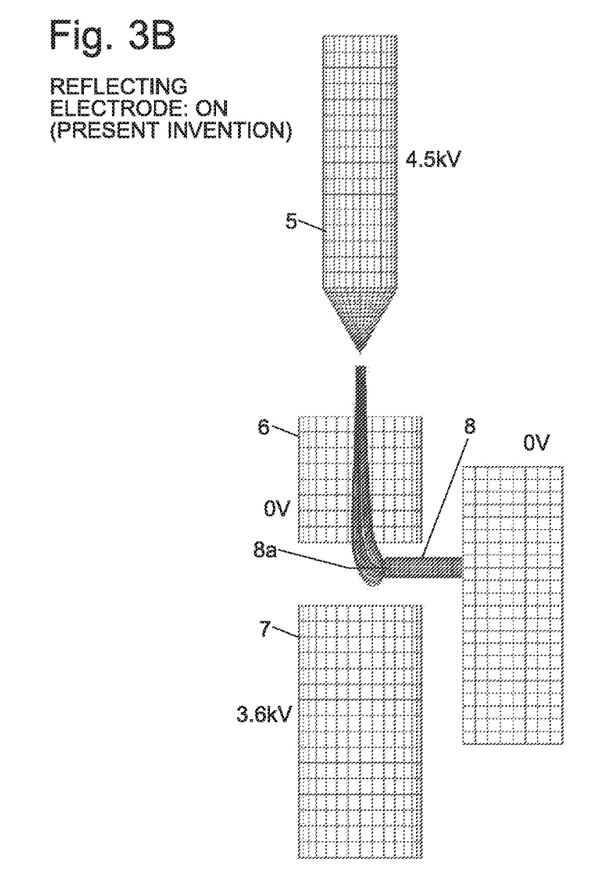
Figure 4A:
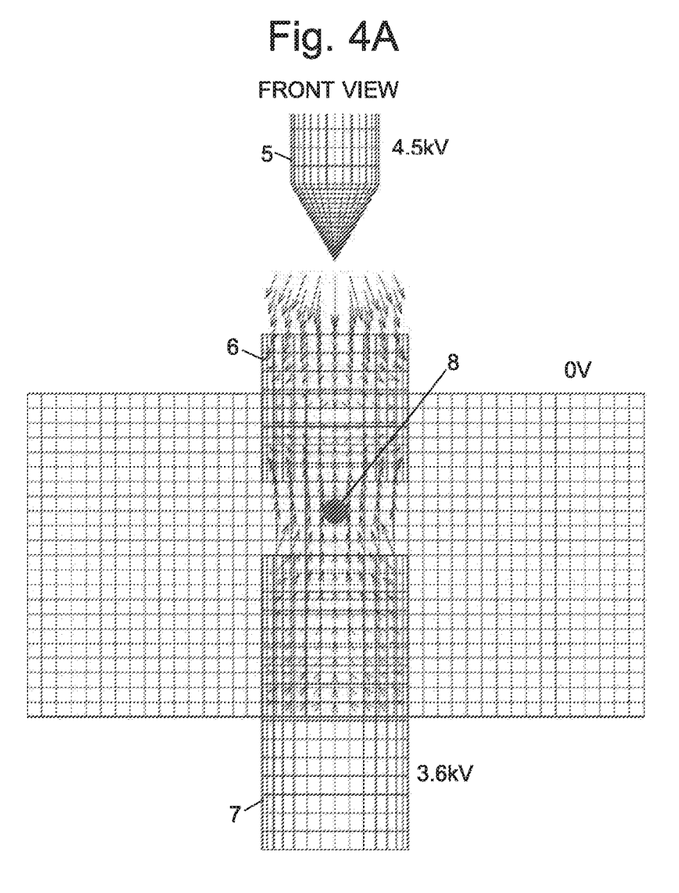
FIGS. 4A and 4B are graphics showing a simulation result of the direction of the forces due to an electric field.
Figure 4B:
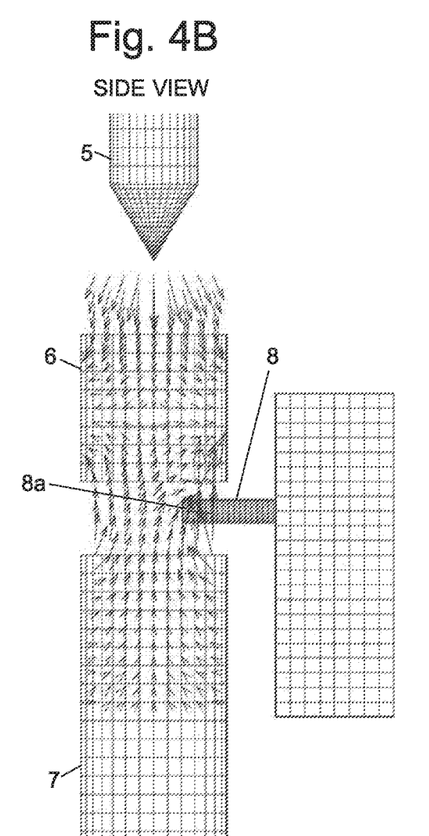
Figure 5A:
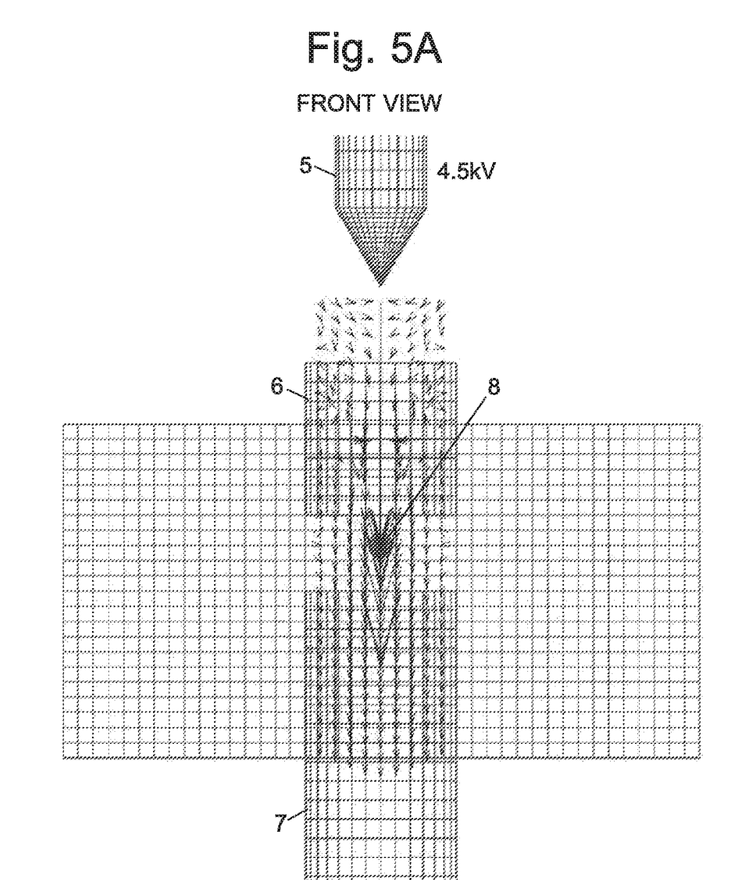
FIGS. 5A and 5B are graphics showing a simulation result of a flow of gas.
Figure 5B:
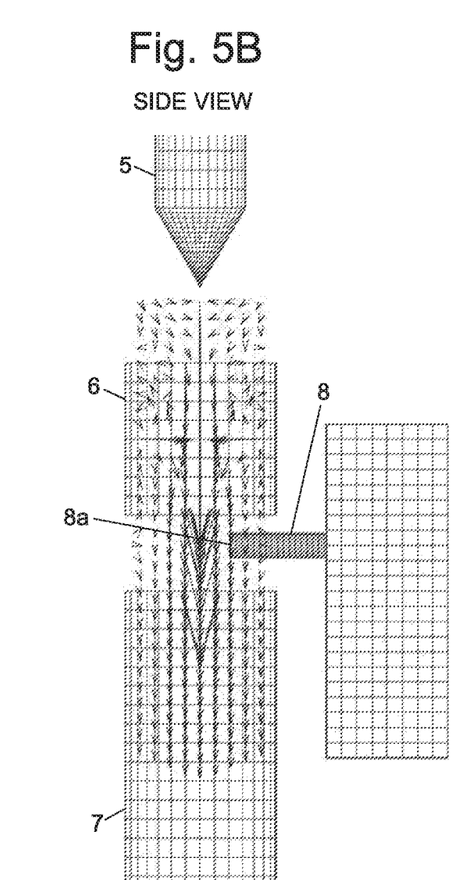

FIGS. 4A and 4B show the simulation result of the direction of the forces due to the electric field. FIGS. 5A and 5B show the simulation result of the gas flow. FIGS. 3A and 3B show the simulation results of the ion trajectories based on equation (1) using the simulation result of the gas flow and that of the electric field. When the reflecting electrode 7 is supplied with no voltage and given the ground potential as with the auxiliary electrode 6, the system can effectively be considered to be equivalent to a prior-art system which has no reflecting electrode 7. FIG. 3A shows the ion trajectories under such a condition, while FIG. 3B shows the ion trajectories under the condition a direct-current voltage of 3.6 kV was applied to the reflecting electrode 7.

As shown in FIG. 3A, when the reflecting electrode 7 is effectively nonexistent, a large number of ions being carried by the flow of gas directly pass by the inlet end 8*a* of the heated capillary 8. By comparison, in the case where the reflecting electrode 7 is used according to the present invention, almost all ions are separated from the gas flow and reflected, to be focused onto the inlet end 8*a* of the heated capillary 8, as shown in FIG. 3B. This result confirms that a large number of ions which would he disposed of in a conventional case can be effectively introduced into the first intermediate vacuum chamber.

Figure 9:
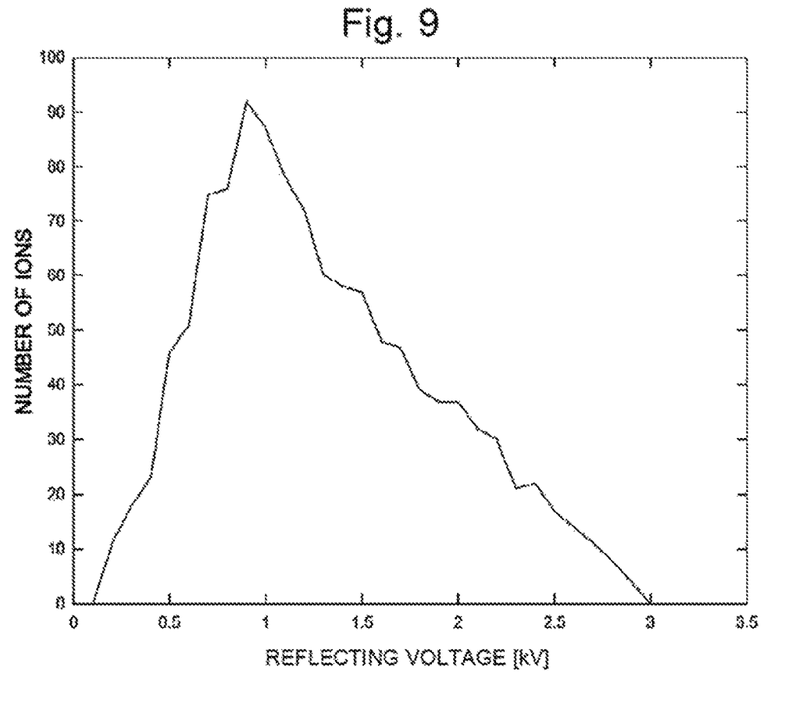
FIG. 9 is a graph obtained by a simulation calculation, showing the relationship between the voltage applied to the reflecting electrode and the number of ions having a specific mass-to-charge ratio which have reached a detection electrode.

In the mass spectrometer of the present embodiment, the efficiency of collecting the ions to the inlet end 8*a* of the heated capillary 8 depends on the strength of the reflecting electric field and the ion mobility. The ion mobility depends on the mass-to-charge ratio of the ion. Therefore, in order to improve the sensitivity of the analysis, it is effective to change the voltage applied to the reflecting electrode 7 according to the mass-to-charge ratio of the ion to he selected by the quadrupole mass filter 12 (i.e. the measurement target ion). FIG. 9 is a graph showing the result of a simulation of the number of ions having a specific mass-to-charge ratio reaching the inlet end 8a of the heated capillary 8 for various values of the voltage applied to the reflecting electrode 7 (reflecting voltage). It can be seen that there is an optimum value of the reflecting voltage for this ion, and a deviation from that optimum value lowers the ion collection efficiency.

Accordingly, in the mass spectrometer according to the present embodiment, for example, the optimum reflecting voltage is experimentally determined beforehand for each of the mass-to-charge ratios of the measurement target ions, and a calculation formula or table showing the relationship between the mass-to-charge ratio and the optimum reflecting voltage is created and stored in the controller 22. When an analysis of a target sample is performed, the controller 22 determines, based on the aforementioned calculation formula or table, the optimum reflecting voltage according to the voltage applied to the quadrupole mass filter 12 (i.e. according to the mass-to-charge ratio of the ion to be selected with the quadruple mass filter 12) and controls the reflecting electrode power source 21 so that the voltage applied to the reflecting electrode 7 becomes equal to the optimum reflecting voltage. In the case where the voltage applied to the quadrupole mass filter 12 is continuously changed to perform a scan measurement over a predetermined range of mass-to-charge ratios, the reflecting voltage is also changed synchronously with the scan operation. As a result, ions are introduced into the first intermediate vacuum chamber 2 and subsequent sections with high efficiency over the entire range of mass-to-charge ratios.

Instead of synchronously changing the voltage applied to the reflecting electrode 7 with the voltage applied to the quadrupole mass filter 12, it is possible to use the auxiliary electrode 6, reflecting electrode 7 and heated capillary 8 as an ion mobility spectrometry unit for changing the mobility of an ion to be monitored, or to use it as an ion mobility filter for selecting ions having a specific mobility. For example, the intensities of various ions which have a specific mass-to-charge ratio yet differ from each other in ion mobility can be determined by continuously changing the voltage applied to the reflecting electrode 7, with the mass-to-charge ratio of the ion to be selected by the quadrupole mass filter 12 fixed. It is also possible to fix the voltage applied to the reflecting electrode 7 and change the mass-to-charge ratio of the ion to be selected by the quadrupole mass filter 12 over a predetermined range of mass-to-charge ratios, so as to investigate the relationship between the mass-to-charge ratio and the ion intensity for ions having a specific ion mobility.

[Second Embodiment]

Figures 6A, 6B:
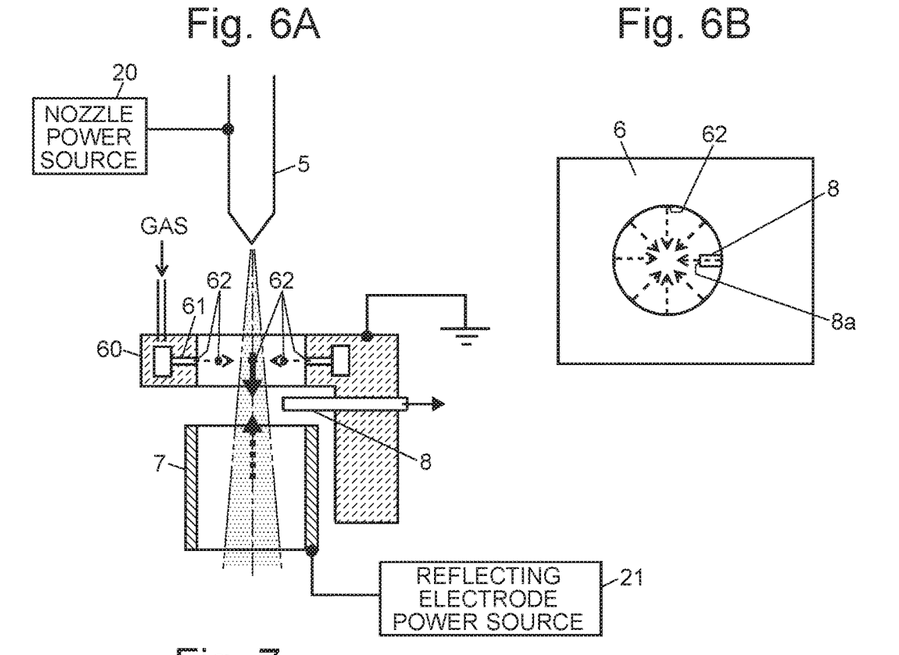
FIGS. 6A and 6B are configuration diagrams of the ion source in a mass spectrometer as the second embodiment of the present invention.

A mass spectrometer which is another embodiment (second embodiment) of the present invention is hereinafter described. FIG. 6A is a configuration diagram of the ion source in the mass spectrometer of the second embodiment. FIG. 6B is a top view of the auxiliary electrode 60. In FIGS. 6A and 6B, the same components as used in the mass spectrometer of the first embodiment are denoted by the same numerals.

In the mass spectrometer of the first embodiment, when the flow velocity of the gas flow ejected from the ionization probe 5 is higher, a higher reflecting voltage is needed to separate ions from the gas flow and repel them. The mass spectrometer of the second embodiment is characterized in that the auxiliary electrode 60 maintained at ground potential is provided with a gas ejection mechanism in order to obtain the ion collection effect with a lower reflecting voltage.

The gas ejection mechanism includes a blocking gas outlet 62 shaped like a slit extending along the entire circumference on the inner circumferential wall of the auxiliary electrode 60, and a gas passage 61 for guiding an externally supplied gas to the blocking gas outlet 62. This gas may be an inert gas similar to the nebulizer gas or the like. As shown in FIG. 6B, the ring-shaped blocking gas outlet 62 ejects the gas toward the cylindrical axis of the auxiliary electrode 60, forming a curtain-like stream of gas blocking the spray flow ejected from the ionization probe 5, in a roughly orthogonal direction to this spray flow. This lowers the flow velocity of the spray flow ejected from the ionization probe 5. Additionally, the ions and charged droplets contained in the spray flow are focused onto an area near the central axis, being prevented from diffusing outwards. This helps the reflecting and focusing electric fields to exhibit their focusing effect.

In the example shown in FIG. 6A, the direction of the gas ejected from the blocking gas outlet 62 is substantially orthogonal to the central axis of the auxiliary electrode 60, i.e. the central axis of the spray flow from the ionization probe 5. Alternatively, the blocking gas outlet 62 may be designed to eject the gas obliquely upward. This makes the gas ejected from the blocking gas outlet 62 move against the spray flow from the ionization probe 5, producing an even higher effect of reduces the gas flow velocity due to the spray flow. However, this configuration unfavorably lowers the effect of focusing the ions and charged droplets in the spray flow onto an area near the central axis. Accordingly, the direction of the blocking gas outlet 62 should be adjusted so that the gas ejected from it collides with the spray flow at an appropriate angle.

[Third Embodiment]

Figure 7:
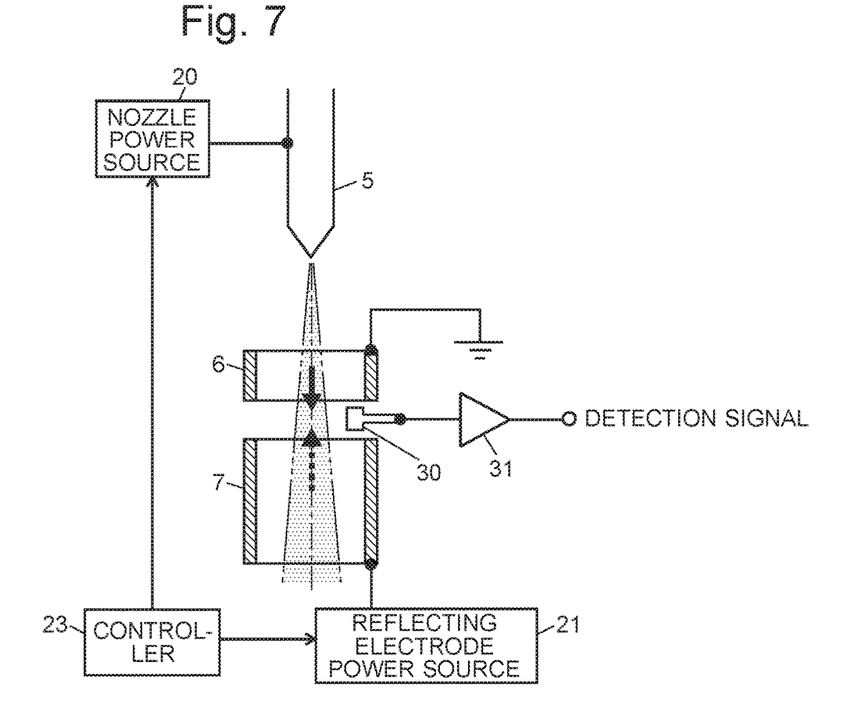
FIG. 7 is a schematic configuration diagram of an ion mobility spectrometer as the third embodiment of the present invention.

An ion mobility spectrometer which is another embodiment (third embodiment) of the present invention is hereinafter described. FIG. 7 is a schematic configuration diagram of the ion mobility spectrometer of the present embodiment.

As already noted, in the configuration shown in FIG. 2, a change in the voltage applied to the reflecting electrode 7 causes a change in the efficiency for an ion having a specific mass-to-charge ratio to reach the inlet end 8a of the heated capillary 8. That is to say, the efficiency of collecting ions to the inlet end 8a of the heated capillary 8 has a dependency on the ion mobility. Making use of this fact, the ion mobility spectrometer of the present embodiment separates and detects ions according to the ion mobility.

In the ion mobility spectrometer of the present embodiment, an ion detection electrode 30 is provided at the location where the inlet end 8a of the heated capillary 8 was located in the mass spectrometer of the first embodiment. An ion current obtained with the ion detection electrode 30 is amplified by an amplifier 31 and provided as a detection signal. When an ion mobility spectrum showing the relationship between the ion mobility and the ion intensity needs to be obtained, the controller 23 operates the reflecting electrode power source 21 so that the voltage applied to the reflecting electrode 7 is continuously changed over a predetermined range. With this operation, the mobility of the ion which can most efficiently reach the ion detection electrode 30 also changes. Therefore, an ion mobility spectrum can be created based on the detection signal. When a temporal change in the ion intensity of the ions having a specific ion mobility needs to be monitored, the controller 23 operates the reflecting electrode power source 21 so that a voltage corresponding to the ion mobility of that ion is applied to the reflecting electrode 7. By this operation, the state in which the ions having that specific ion mobility can most efficiently reach the ion detection electrode 30 is maintained. Therefore, a chromatogram for ions having that specific ion mobility can be created based on the detection signal.

Conventional ion mobility spectrometers can separate ions with high resolving power according to the ion mobility. However, those systems are large in scale due to such factors as a complex electrode configuration for creating electric fields as well as a complex structure for generating a gas flow with a constant flow velocity. By comparison, in the ion mobility spectrometer of the present embodiment, the section for separating ions according to their mobility has an extremely simple configuration and allows for the realization of a small and inexpensive device. Therefore, for example, a system which is suitable as an option for a detector for liquid chromatographs can be provided.

[Fourth Embodiment]

Figure 8:
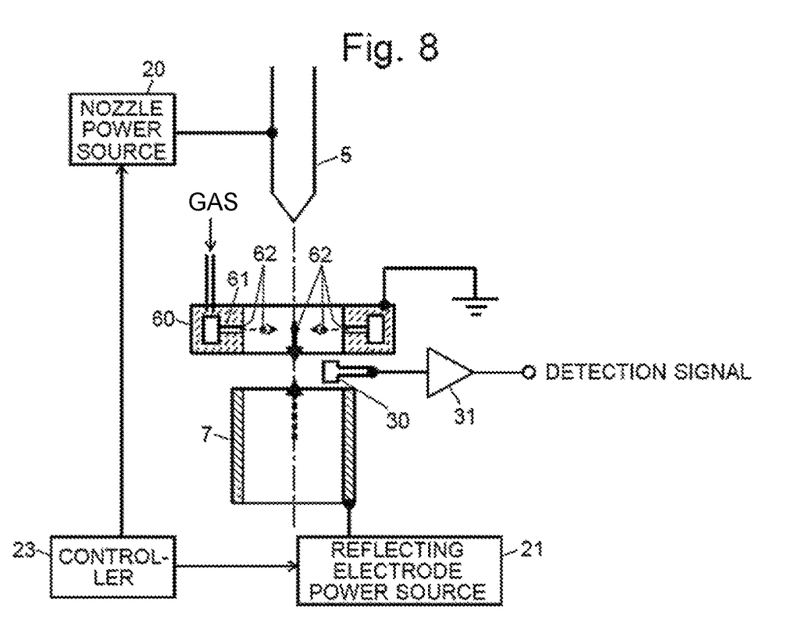
FIG. 8 is a schematic configuration diagram of an ion mobility spectrometer as the fourth embodiment of the present invention.

FIG. 8 is an ion mobility spectrometer in which the ion detection electrode 30 is provided at the location where the inlet end 8a of the heated capillary S was located in the mass spectrometer of the second embodiment shown in FIGS. 6A and 6B. Similarly to the mass spectrometer of the second embodiment, in the ion mobility spectrometer of the fourth embodiment, when the flow velocity of the spray flow ejected from the ionization probe 5 is high, the flow velocity can be reduced by the effect of the curtain-like blocking gas, allowing the voltage applied to the reflecting electrode 7 to be decreased.

It should be noted that any of the previous embodiments is a mere example of the present invention, and any change, modification or addition appropriately made within the spirit of the present invention will naturally fall within the scope of claims of the present application.

REFERENCE SIGNS LIST

1 . . . Ionization Chamber
2 . . . First Intermediate Vacuum Chamber
3 . . . Second Intermediate Vacuum Chamber
4 . . . Analysis Chamber
5 . . . Ionization Probe
6, 60 . . . Auxiliary Electrode
61 . . . Gas Passage
62 . . . Blocking Gas Outlet
7 . . . Reflecting Electrode
8 . . . Heated Capillary
8a . . . Inlet End
9 . . . Ion Guide
10 . . . Skimmer
11 . . . Ion Guide
12 . . . Quadrupole Mass Filter
13 . . . Ion Detector
20 . . . Nozzle Power Source
21 . . . Reflecting Electrode Power Source
22, 23 . . . Controller

The invention claimed is:

1. A mass spectrometer provided with: an ion source including an ionization probe for spraying a liquid sample into an ionization chamber in which an ambience of atmospheric pressure is present; and an ion introduction section for sending, from the ionization chamber to a vacuum chamber, ions generated by the ion source from a component contained in sample droplets sprayed from the ionization probe, where an arrangement of the ionization probe and the ion introduction section is determined so that a spraying direction of the liquid sample from the ionization probe extends orthogonally or obliquely to a direction of introducing the ions from the ionization chamber by the ion introduction section, the mass spectrometer comprising:

a) an auxiliary electrode provided in the spraying direction of the sample droplets from the ionization probe and at a closer position to the ionization probe than an inlet end of the ion introduction section, the auxiliary electrode surrounding a central axis of a spray flow from the ionization probe;

b) a reflecting electrode provided in the spraying direction of the sample droplets from the ionization probe and at a farther position to the ionization probe than the inlet end of the ion introduction section, the reflecting electrode having a hollow cylindrical shape with a through-hole through which the central axis of the spray flow from the ionization probe passes; and c) a voltage supplier for applying, to the reflecting electrode, a voltage determined with reference to a potential of the auxiliary electrode so that a measurement target ion is reflected by the reflecting electrode.

2. The mass spectrometer according to claim 1, wherein:
the auxiliary electrode is equipped with a gas ejector for ejecting gas from outside the spray flow ejected from the ionization probe, toward the central axis of the same spray flow, in a manner to surround the spray flow by the gas.

3. The mass spectrometer according to claim 1, wherein:
the voltage supplier changes the applied voltage to the reflecting electrode according to a mass-to-charge ratio of the measurement target ion.

4. An ion mobility spectrometer comprising:

a) an ion source including an ionization probe for spraying a liquid sample into an ambience of atmospheric pressure;

b) an ion detector located anterior to a spray flow from the ionization probe, for detecting ions generated by the ion source from a component contained in sample droplets sprayed from the ionization probe;

c) an auxiliary electrode provided in a spraying direction of the sample droplets from the ionization probe and at a closer position to the ionization probe than the ion detector, the auxiliary electrode surrounding a central axis of a spray flow from the ionization probe;

d) a reflecting electrode provided in the spraying direction of the sample droplets from the ionization probe and at a farther position to the ionization probe than the ion detector, the reflecting electrode having a hollow cylindrical shape with a through-hole through which the central axis of the spray flow from the ionization probe passes; and e) a voltage supplier for applying, to the reflecting electrode, a voltage determined with reference to a potential of the auxiliary electrode so that a measurement target ion is reflected by the reflecting electrode.

5. The ion mobility spectrometer according to claim 4, wherein:
the auxiliary electrode is equipped with a gas ejector for ejecting gas from outside the spray flow ejected from the ionization probe, toward the central axis of the same spray flow, in a manner to surround the spray flow by the gas.

6. The mass spectrometer according to claim 2, wherein:
the voltage supplier changes the applied voltage to the reflecting electrode according to a mass-to-charge ratio of the measurement target ion.

7. The ion mobility spectrometer according to claim 4, wherein:
the ion detector is located directly between the auxiliary electrode and the reflecting electrode.

8. The mass spectrometer according to claim 2, wherein:
the gas ejector is configured to eject the gas obliquely upward toward the central axis of the spray flow.

9. The ion mobility spectrometer according to claim 5, wherein:
the gas ejector is configured to eject the gas obliquely upward toward the central axis of the spray flow.

10. A mass spectrometer provided with: an ion source including an ionization probe for spraying a liquid sample into an ionization chamber in which an ambience of atmospheric pressure is present; and an ion introduction section for sending, from the ionization chamber to a vacuum chamber, ions generated by the ion source from a component contained in sample droplets sprayed from the ionization probe, where an arrangement of the ionization probe and the ion introduction section is determined so that a spraying direction of the liquid sample from the ionization probe extends orthogonally or obliquely to a direction of introducing the ions from the ionization chamber by the ion introduction section, the mass spectrometer comprising:

a) an auxiliary electrode provided in the spraying direction of the sample droplets from the ionization probe and at a closer position to the ionization probe than an inlet end of the ion introduction section, the auxiliary electrode surrounding a central axis of a spray flow from the ionization probe;

b) a reflecting electrode provided in the spraying direction of the sample droplets from the ionization probe and at a farther position to the ionization probe than the inlet end of the ion introduction section, the reflecting electrode surrounding the central axis of the spray flow from the ionization probe; and c) a voltage supplier for applying, to the reflecting electrode, a voltage determined with reference to a potential of the auxiliary electrode so that a measurement target ion is reflected by the reflecting electrode, wherein the voltage supplier changes the applied voltage to the reflecting electrode according to a mass-to-charge ratio of the measurement target ion.

* * * * *